United States Patent [19]

Green et al.

[11] Patent Number: 5,344,059
[45] Date of Patent: Sep. 6, 1994

[54] SURGICAL APPARATUS AND ANVIL DELIVERY SYSTEM THEREFOR

[75] Inventors: David T. Green, Westport; Henry Bolanos, East Norwalk; Henry R. Sienkiewicz, Stamford, all of Conn.; Patrick Leahy, Dublin, Ireland

[73] Assignee: United States Surgical Corporation, Norwalk, Conn.

[21] Appl. No.: 950,435

[22] Filed: Sep. 23, 1992

Related U.S. Application Data

[63] Continuation-in-part of Ser. No. 886,040, May 19, 1992.

[51] Int. Cl.⁵ .......................................... A61B 17/115
[52] U.S. Cl. ...................................... 227/179; 227/19
[58] Field of Search ................. 227/19, 179, 175, 176, 227/178

[56] References Cited

U.S. PATENT DOCUMENTS

| | | |
|---|---|---|
| 3,193,165 | 7/1965 | Akhalaya et al. . |
| 3,593,903 | 7/1971 | Astafiev et al. . |
| 4,198,982 | 4/1980 | Fortner et al. . |
| 4,304,236 | 12/1981 | Conta et al. . |
| 4,319,576 | 2/1986 | Rothfuss . |
| 4,379,457 | 4/1983 | Gravener et al. . |
| 4,473,077 | 9/1984 | Noiles et al. . |
| 4,476,863 | 10/1984 | Kanshin et al. . |
| 4,505,272 | 3/1985 | Utyamyshev . |
| 4,537,193 | 8/1985 | Tanner . |
| 4,566,620 | 1/1986 | Green et al. ..................... 227/19 |
| 4,573,468 | 3/1986 | Conta et al. . |
| 4,576,167 | 3/1986 | Noiles . |
| 4,603,693 | 8/1986 | Conta et al. . |
| 4,646,745 | 3/1987 | Noiles . |
| 4,671,445 | 6/1987 | Barker et al. ..................... 227/19 |
| 4,817,847 | 4/1989 | Redtenbacher et al. . |
| 4,848,367 | 7/1989 | Avant et al. . |
| 4,873,977 | 10/1989 | Avant et al. . |
| 5,104,025 | 4/1992 | Main et al. . |
| 5,108,420 | 4/1992 | Marks . |
| 5,119,983 | 6/1992 | Green et al. . |
| 5,122,156 | 6/1992 | Green et al. . |
| 5,139,513 | 8/1992 | Segato ........................... 227/179 X |
| 5,271,543 | 12/1993 | Grant et al. ...................... 227/19 X |

FOREIGN PATENT DOCUMENTS

| | | |
|---|---|---|
| 1136020 | 12/1979 | Canada . |
| 0190022 | 8/1986 | European Pat. Off. . |
| 282157 | 9/1988 | European Pat. Off. . |
| 1057729 | 5/1959 | Fed. Rep. of Germany . |
| 3301713 | 7/1984 | Fed. Rep. of Germany . |
| 1461464 | 12/1966 | France . |
| 1588250 | 4/1970 | France . |
| 2443239 | 12/1979 | France . |
| 7711347 | 4/1979 | Netherlands . |
| WO8706448 | 11/1987 | PCT Int'l Appl. . |
| WO9006085 | 6/1990 | PCT Int'l Appl. . |

OTHER PUBLICATIONS

"Use of the Stapler in Interior Reception for Cancer of the Rectosigmoid", Resnick et al., *Israel Journal of Medical Sciences*, vol. 19, 1983, pp. 128–133.
"New Method of Bowel Stoma Formation", *American Journal of Surgery*, vol. 152, Nov. 1986, pp. 545–548.
EEA Anvil with a Separate Short-Shaft-Non Confidential Disclosure Agreement-Sep. 1981.
"Minimally Invasive Colon Resection (Laparoscopic Colectomy)", Jacobs et al., *Surgical Laparoscopy & Endoscopy*, vol. 1, No. 3, Sep. 1991, pp. 144–150.
U.S. Surgical Corporation, "Auto Suture Information Booklet" 1990.

*Primary Examiner*—Rinaldi I. Rada

[57] ABSTRACT

A detachable anvil assembly for use with an apparatus for performing circular anastomosis of tubular organs includes an elongated anvil rod having proximal and distal end portions and an anvil head mounted to the distal end portion of the anvil rod. The distal end portion is pivotally mounted and is adapted to pivot approximately plus or minus ninety degrees relative to a longitudinal axis defined by the rod. An elongated delivery member detachably receives the anvil assembly and facilitates delivery of the anvil assembly to the operative site. The pivoting feature of the distal end reduces the transverse profile of the assembly which consequently facilitates introduction and advancement of the anvil assembly within the tubular organ.

15 Claims, 6 Drawing Sheets

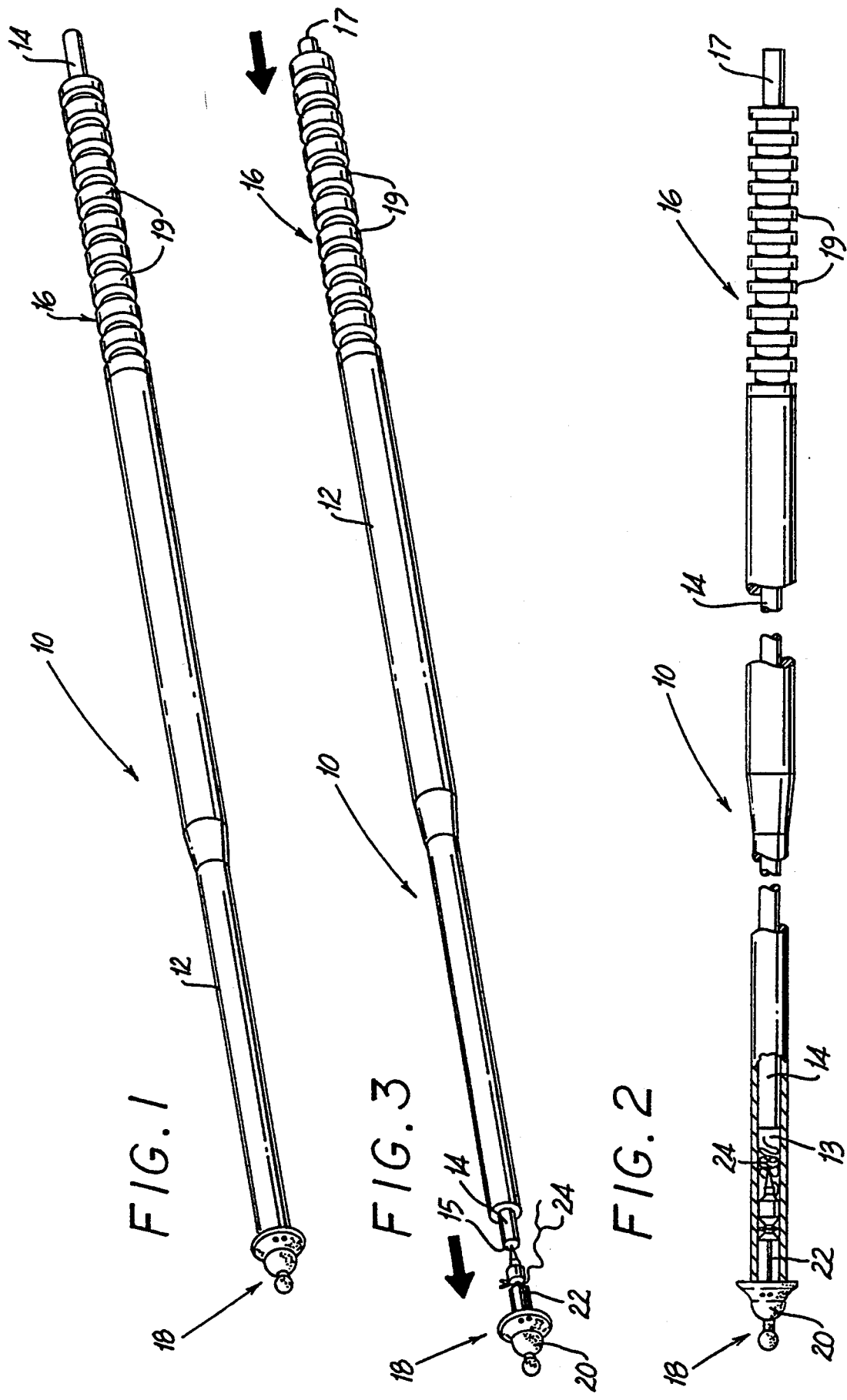

SURGICAL APPARATUS AND ANVIL DELIVERY SYSTEM THEREFOR

CROSS REFERENCE TO RELATED APPLICATION

This is a continuation-in-part of copending application Ser. No. 07/886,040, filed May 19, 1992.

BACKGROUND OF THE INVENTION

1. Field of the Invention

The present invention relates generally to an apparatus for performing circular anastomosis of hollow tissue organs and more particularly to an anvil delivery system for use with the apparatus to facilitate introduction and manipulation of an anvil through hollow organ tissue.

2. Description of the Prior Art

Anastomosis is the surgical joining of separate hollow organ sections so that the sections intercommunicate with each other. Typically, the anastomosis procedure follows surgery in which a diseased or defective section of hollow tissue is removed and the remaining end sections are to be joined. Depending on the desired anastomosis procedure, the end sections may be joined by either circular, end-to-side or side-to-side organ reconstruction methods.

In a circular anastomosis procedure, the two ends of the organ sections are joined by means of a stapling instrument which drives a circular array of staples through the end sections and simultaneously cores any overlapping tissue to free the tubular passage.

Examples of instruments for performing circular anastomosis of hollow organs are described in U.S. Pat. Nos. 4,304,236, 4,379,457, 4,573,468, 4,576,167, 4,603,693, 4,646,745, 5,119,983 and 5,122,156. These instruments typically include an elongated shaft having a handle portion at a proximal end to actuate the instrument and a staple holding component disposed at a distal end. An anvil assembly including an anvil rod with attached anvil head is mounted to the distal end. Opposed end portions of the organs to be stapled are clamped between the anvil head and the staple holding component. The clamped tissue is stapled by driving one or more staples from the staple holding component so that the ends of the staples pass through the tissue and are clinched by the anvil head.

In some applications of the circular anastomosis procedure, the anvil rod with attached anvil head is mounted to the distal end of the shaft prior to insertion of the instrument into the tissue to be anastomosed. However, in other applications, it is preferable to utilize a detachable anvil rod which may be mounted to the instrument subsequent to positioning of the instrument and the anvil assembly within their respective tissue sections. In such instances, the stapling instrument and the anvil assembly are separately applied to the operative site. Each tissue section is then secured to their respective anvil or staple holding component by a purse string. The anvil assembly is mounted to the surgical instrument by inserting a mounting portion of the anvil rod within the distal end of the instrument so that a mounting mechanism within the instrument securely engages the rod. Preferably, preparation of the tissue sections to be joined and mounting of the anvil rod to the instrument are performed using minimally invasive surgical techniques, i.e., under laparoscopic guidance.

A particular difficulty concerning the aforedescribed approach to perform anastomosis of hollow body organs with a detachable anvil assembly, whether the anastomosis is performed laparoscopically or by conventional surgical techniques, concerns delivery and placement of the anvil assembly at the desired location within the hollow organ. This difficulty is attributed to, inter alia, the fact that the anvil assembly, particularly, the mounted anvil head, presents an obtrusive profile which engages the inner wall of the hollow organ during advancement therethrough. In some instances, the dimension of the anvil head is greater than the cross-sectional dimension of the hollow organ in which it must pass. Consequently, advancement of the anvil assembly through the hollow organ is impeded or possibly prevented. Furthermore, if surgery is being performed laparoscopically, difficulty with maneuvering the anvil assembly through the hollow organ may necessitate an abandonment of such laparoscopic approach and a conversion to a conventional laparotomy to complete the anastomosis.

Accordingly, the present invention is directed to an anvil rod and related applications, which rod and associated structures facilitate delivery of the rod through organ tissue and maneuvering of the rod about the operative site. The structure also facilitates use of the rod in endoscopic and laparoscopic procedures.

SUMMARY OF THE INVENTION

Generally stated, the present invention is directed to an anvil assembly and associated delivery system, the anvil assembly being adapted for use with an apparatus for performing circular anastomosis. The anvil assembly comprises an elongated anvil rod having proximal and distal end portions and an anvil head detachably mounted to the distal end portion of the anvil rod. The distal end portion is pivotally mounted and is adapted to pivot from a first operative position to a second non-operative position, whereby at least one dimension of the anvil assembly in the second non-operative position is effectively less than the corresponding dimension in the first operative position.

In a preferred embodiment, the anvil assembly comprises an elongated anvil rod having proximal and distal end portions and an anvil head detachably mounted to the distal end portion of the anvil rod. The distal end portion is pivotal from a first operative position in general alignment with a longitudinal axis defined by the anvil rod to a second non-operative position angularly displaced relative to the longitudinal axis. In the second non-operative position, the anvil rod presents a less obtrusive profile which, accordingly, facilitates advancement of the anvil assembly through body tissue.

The distal end portion is pivotal with respect to the longitudinal axis defined by the anvil rod through an angle of up to about 90°. In particular, the distal end portion is adapted to pivot up to about 90° with respect to each side of the longitudinal axis, thereby providing full pivotal articulation thereof of about 180°.

The distal end portion comprises a circumferential mounting collar which is received within a circular aperture formed within the anvil head to mount the anvil head to the anvil rod. The mounting collar preferably comprises a plurality of longitudinally extending external splines which are engagable with cooperating longitudinally extending internal splines formed within the anvil head to properly align the anvil head with the anvil rod.

The anvil rod also comprises a plurality of longitudinally extending external splines disposed intermediate its proximal and distal end portions. The external splines are engagable with cooperating longitudinally extending internal splines formed within a distal end of the apparatus to properly align the anvil rod with the apparatus.

The anvil apparatus is adapted to be mounted to an elongated delivery member which includes a mounting mechanism for detachably mounting the anvil assembly on a distal end of the elongated delivery member and releasing means for releasing the anvil member from the mounting means. A preferred delivery member is disclosed and described in copending commonly assigned U.S. patent application Ser. No. 07/886,040, filed May 19, 1992, the entire contents of which are incorporated herein by reference.

The present invention is also directed to a surgical apparatus for performing circular anastomosis of first and second tissue sections. The apparatus comprises elongated tubular means having a proximal and a distal end, means for firing a plurality of fasteners from the distal end of the elongated tubular means and anvil means detachably mounted to the distal end of the elongated tubular means. The anvil means comprises an anvil rod having proximal and distal end portions and an anvil head detachably mounted to the distal end portion of the anvil rod. The distal end portion is pivotal from a first operative position in general alignment with a longitudinal axis defined by the anvil rod to a second non-operative position angularly displaced relative to the longitudinal axis. The anvil assembly defines an effective cross-sectional area generally transverse to the longitudinal axis. The effective cross-sectional area of the anvil assembly in the second non-operative position is less than the effective cross-sectional area of the anvil assembly in the first operative position to facilitate introduction and advancement of the anvil assembly through body tissue.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figure 1:
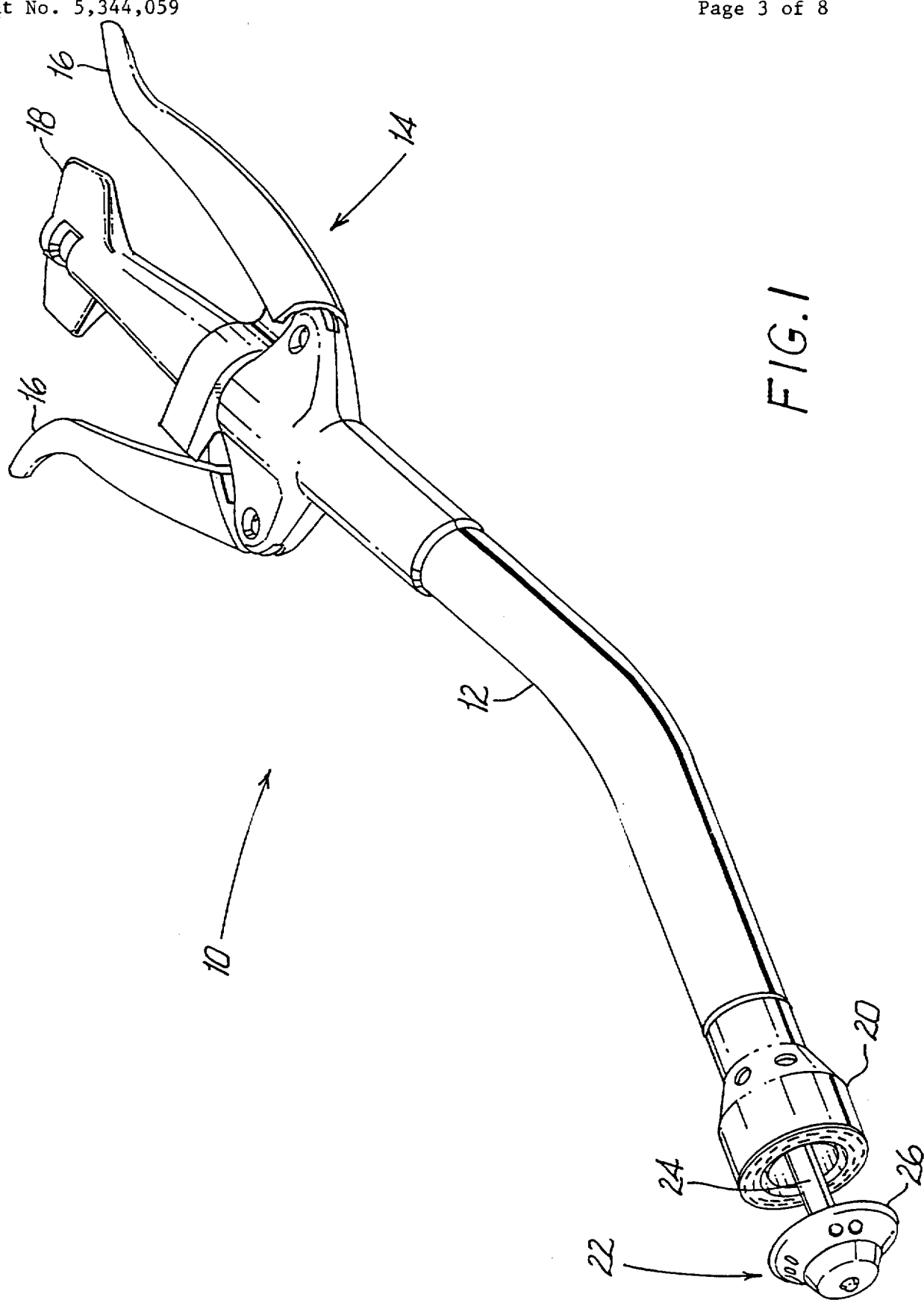
FIG. 1 is a perspective view of a surgical stapler apparatus for performing anastomosis of hollow organs of the type contemplated by the present invention.

Referring initially to FIG. 1, there is illustrated an apparatus 10 for stapling hollow tubular body organs as by circular anastomosis of intestines, colons, or the like. The apparatus may be utilized to attach two tubular body parts or one tubular body part to a non-tubular body part by circular anastomosis and may be adapted to attach the body parts with deformable metallic staples or bio-absorbable two-part body tissue fasteners.

Such apparatus 10 is disclosed and claimed in U.S. Pat. No. 5,119,983, issued Jun. 9, 1992, which is incorporated by reference herein and made a part of this disclosure. This apparatus is a stapler for anastomosis of hollow body organs such as intestines, colons, etc. Other such devices are disclosed in the following U.S patents which are also incorporated by reference herein and made a part of this disclosure: U.S. Pat. No. 4,304,236, issued Dec. 8, 1981; U.S. Pat. No. 4,379,457, issued Apr. 12, 1983; U.S. Pat. No. 4,573,468, issued Mar. 4, 1986; U.S. Pat. No. 4,576,167, issued Mar. 18, 1986; U.S. Pat. No. 4,603,693, issued Aug. 5, 1986; U.S. Pat. No. 4,646,745, issued Mar. 3, 1987 and U.S. Pat. No. 5,122,156, issued Jun. 16, 1992. As will be appreciated from a review of these patents, such devices in some instances may also be manually operated and are sometimes controlled from a location remote from the point of manipulation.

Generally, apparatus 10 includes elongated shaft 12 and handle mechanism 14 attached to a proximal end of the elongated shaft. Handle mechanism 14 includes actuating handles 16 and adjusting wing nut 18. Fastener retainer component 20 is connected to the distal end of shaft 12 and houses an annular array of staples therein. A staple firing mechanism expels the staples from fastener retainer component 20.

An anvil assembly 22 is detachably mounted to the distal end of elongated shaft 12 by a mounting mechanism within the shaft which cooperatively engages the anvil assembly. Anvil 22 includes detachable anvil rod 24 with attached anvil head 26. Anvil head 26 includes staple receiving buckets (not shown) for receiving and clinching the staples expelled by the staple firing mechanism to thereby join the adjacent tissue sections.

Figure 2:
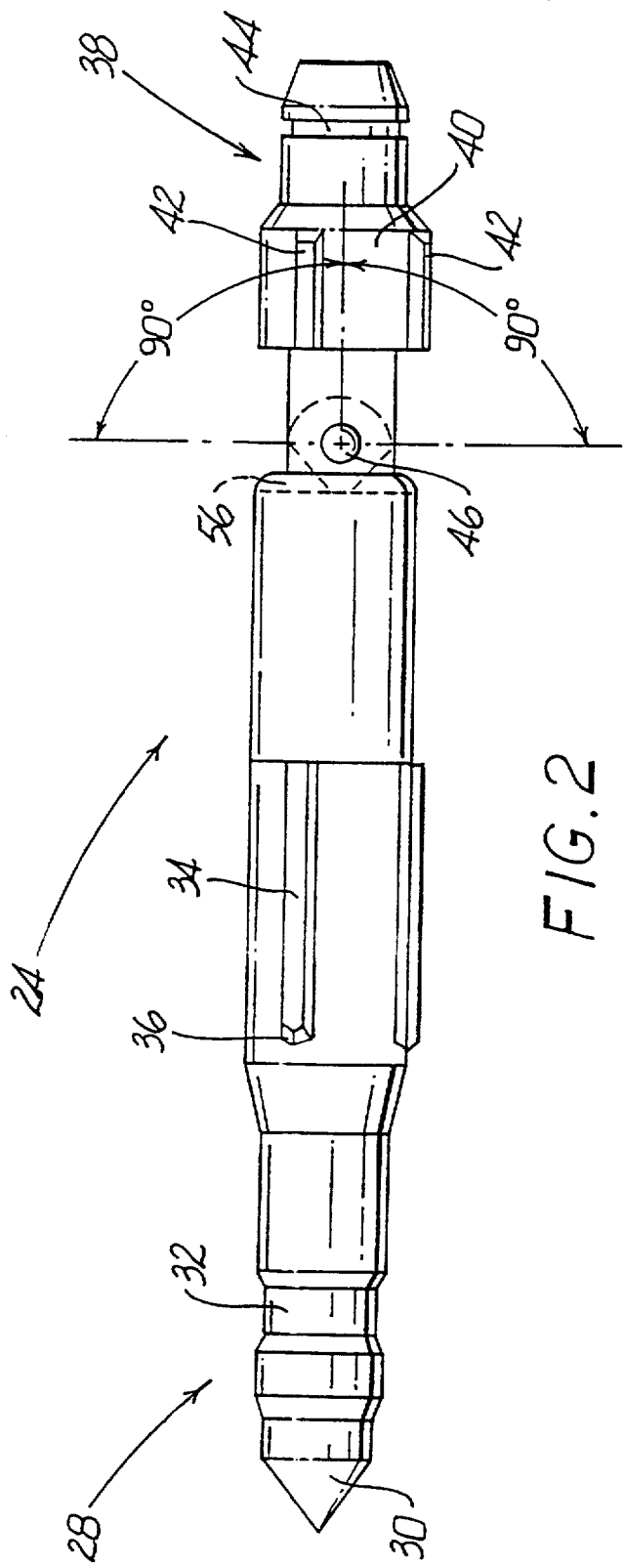
FIG. 2 is a side plan view of the detachable anvil rod constructed according to the present invention illustrating the pivotal distal end portion.

Referring now to FIG. 2, there is illustrated the detachable anvil rod 24 constructed according to the present invention. Anvil rod 24 is adapted to be used with apparatus 10 and includes proximal end portion 28 which is received within and engages the mounting mechanism within the distal end of elongated shaft 12. (FIG. 1) Proximal end portion 28 includes a generally conical shaped mounting portion 30 which is advantageously dimensioned to facilitate entry within the distal end of apparatus 10 and which further enables manipulation of rod 24 through body tissue. Proximal end portion 28 also includes an annular recess 32 which is correspondingly configured to be engaged by the mounting mechanism within the distal end of elongated shaft 12 of the apparatus.

A plurality of longitudinally extending external splines 34 are disposed in the general midportion of anvil rod 24. Splines 34 engage correspondingly configured and positioned longitudinal internal splines in the distal end of elongated shaft 12 during mounting of the rod to the apparatus to ensure proper alignment of the rod with the staple firing mechanism. Each external spline 34 has a chamfered and sloped proximal end 36. Chamfered ends 36 engage the internal splines within elongated shaft 12 and cause the rod to rotate slightly if the internal and external splines are initially misaligned during mounting so as to ensure proper mating between the two components.

Distal end portion 38 of anvil rod 24 includes an anvil head mounting collar 40 for mounting anvil head 26 to the rod. Collar 40 includes a plurality of longitudinally extending external splines 42 which engage with cooperating longitudinally extending internal splines in the anvil head 26 to properly align the staple-receiving buckets in the anvil head with the staples in fastener retainer component 20. A circumferential groove 44 is formed adjacent collar 40 and is adapted to receive a U-shaped clamp which securely retains the anvil head on the collar.

Figure 3:
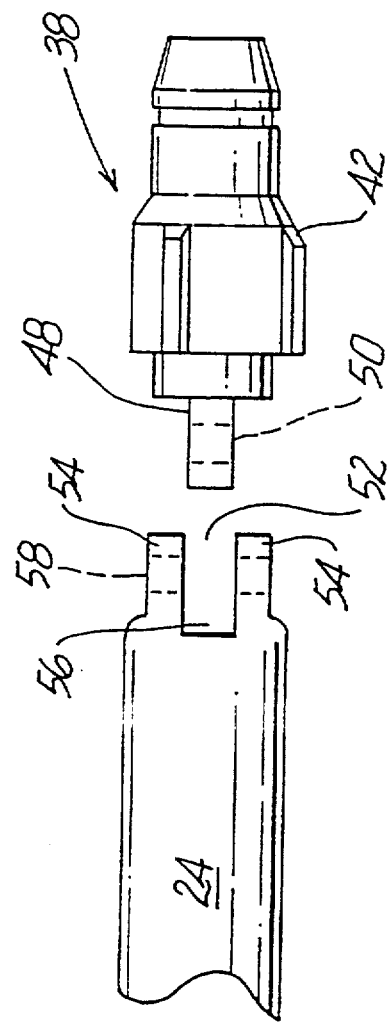
FIG. 3 is a sectional view with parts separated of the distal end portion and the remaining portion of the rod illustrating the mounting components for pivotally mounting the distal end portion.
Figure 4:
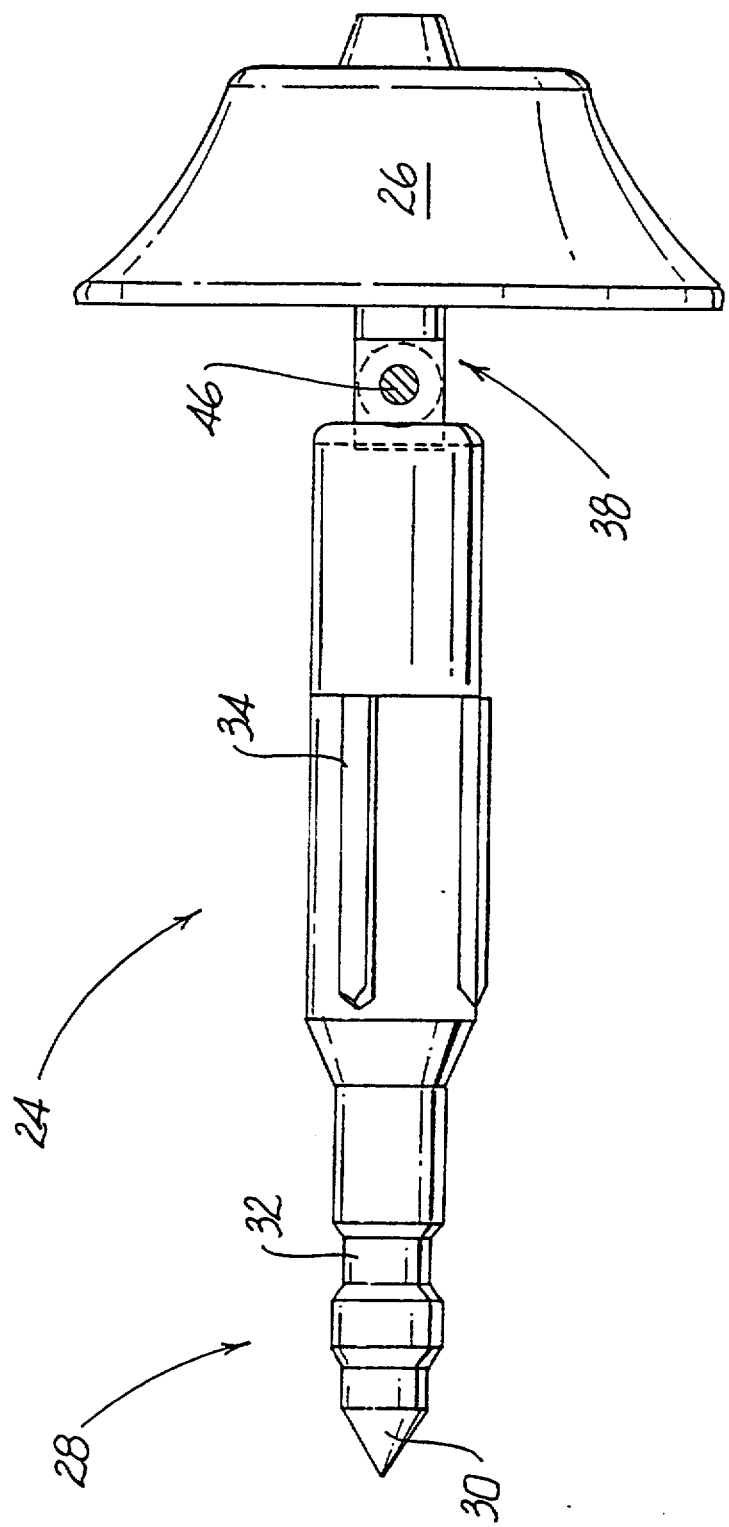

Distal end portion 38 of anvil rod 24 is pivotally mounted about pivoting pin 46 and is adapted to pivot from a position in general alignment with the remainder of rod 24 through pivoted locations (shown by the arrows) corresponding to plus or minus 90 degrees. As best shown in FIG. 3, distal end portion 38 includes a projecting member 48 having a generally circular aperture 50 (shown in phantom), which member 48 is received within a recess 52 defined between two correspondingly dimensioned and positioned projection members 54 extending from the main portion of rod 24. Preferably, a slight groove 56 is formed in the main portion of rod adjacent recess 52 to accommodate projecting member 48 during pivoting action of distal end portion 38. Projections 54 also include apertures 58 (shown in phantom) which align with aperture 50 formed in projecting member 48 of distal end portion 38 to receive pivoting pin 46 to effect the mounting. Other alternative methods for mounting distal end portion 38 to the main portion of rod 24 may be readily determined by one skilled in the art.

Figure 4:
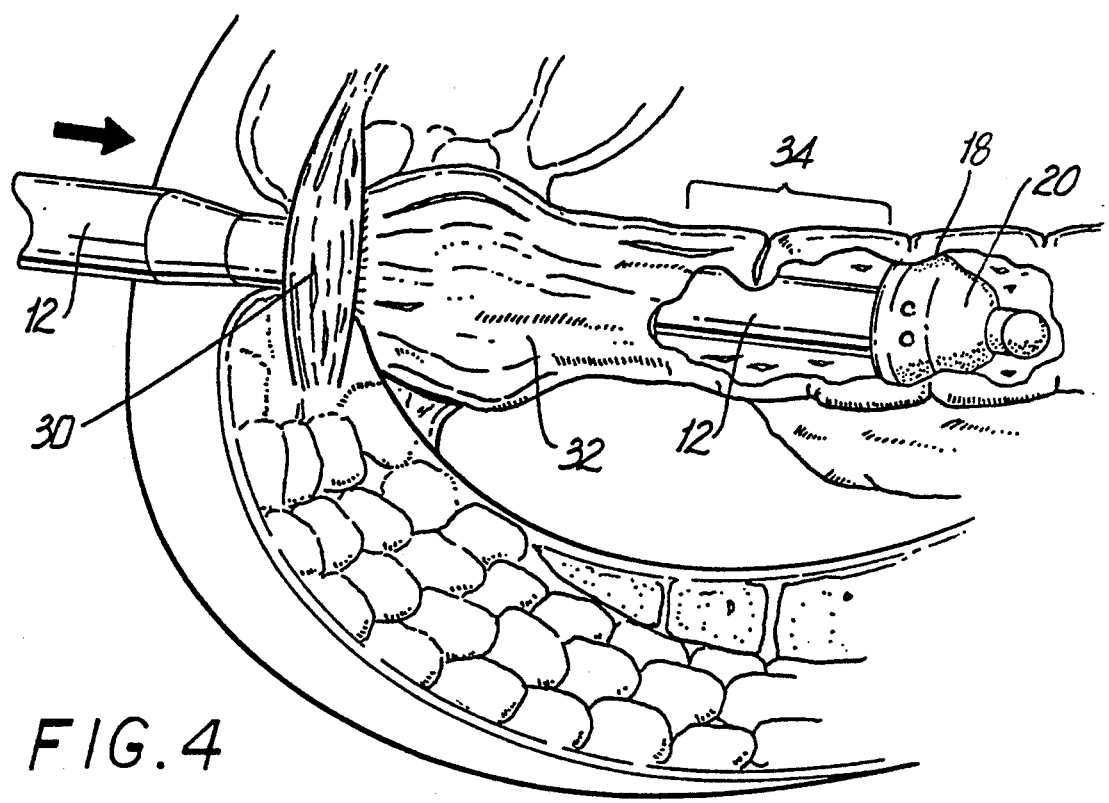
FIG. 4 is a side plan view of the detachable anvil rod of FIG. 2 with mounted anvil head illustrating the distal end portion of the rod in a generally aligned operative position.
Figure 5:
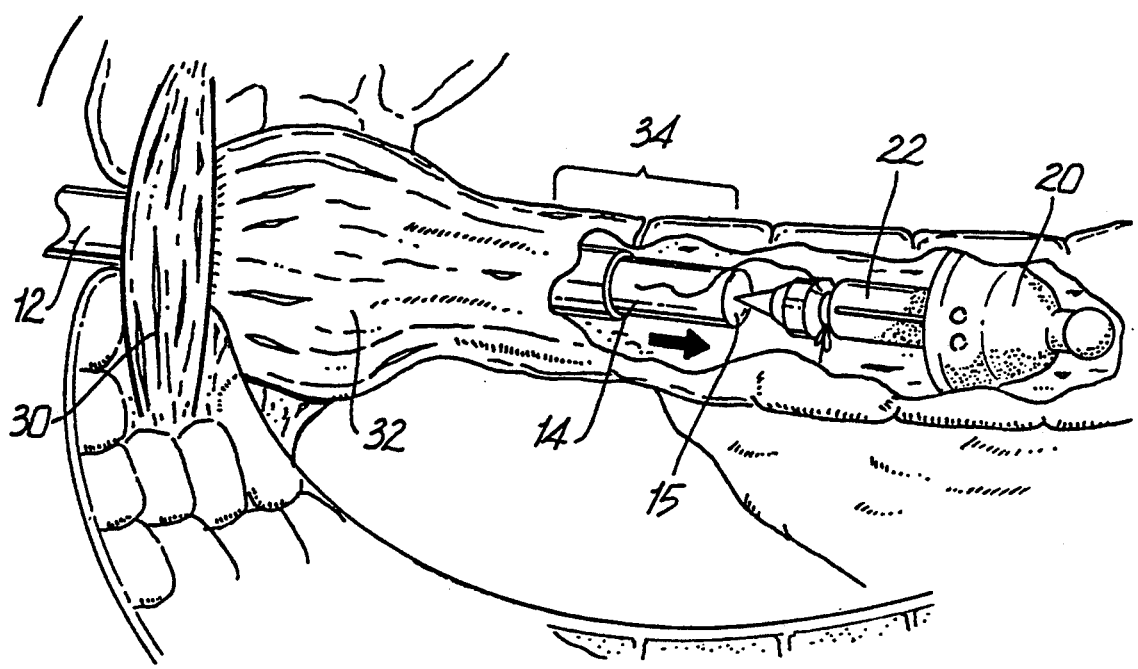
FIGS. 5A–5B are side plan views similar to the view of FIG. 4 illustrating the distal end portion of the anvil rod pivoted 90° with respect to each side of the longitudinal axis defined by the anvil rod.
Figure 5A:
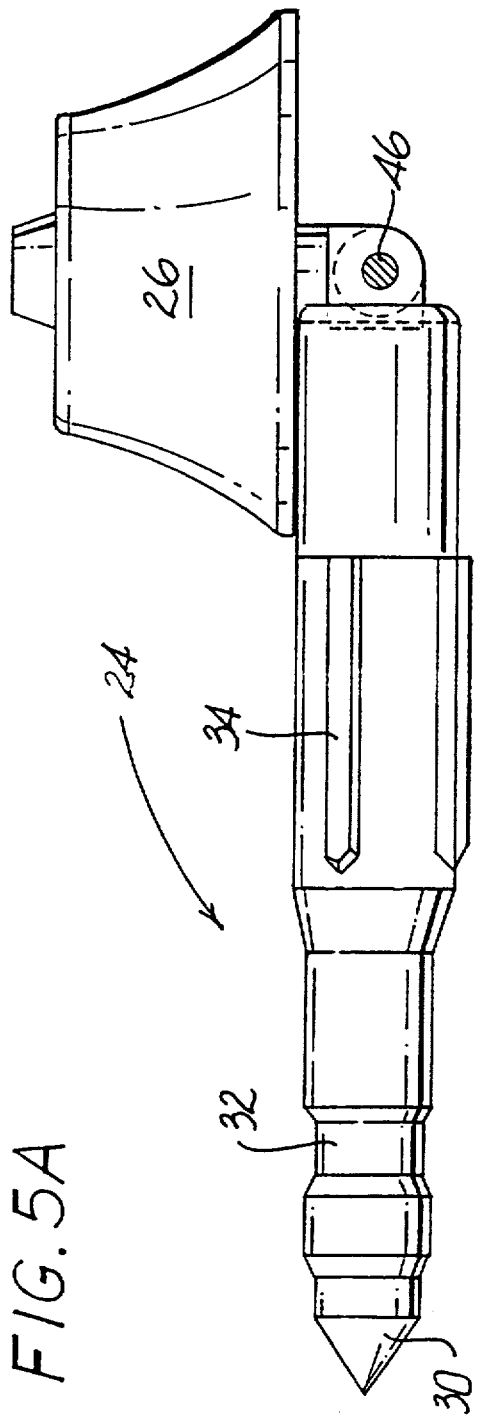
Figure 5B:
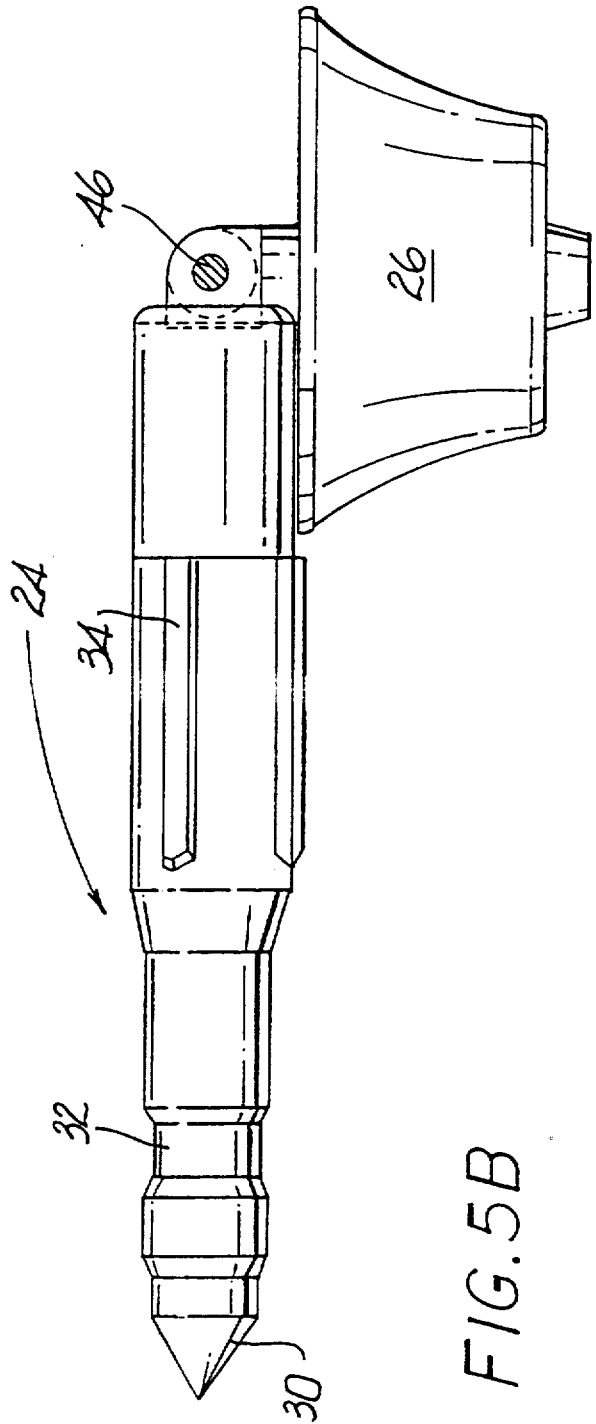
Figure 6:
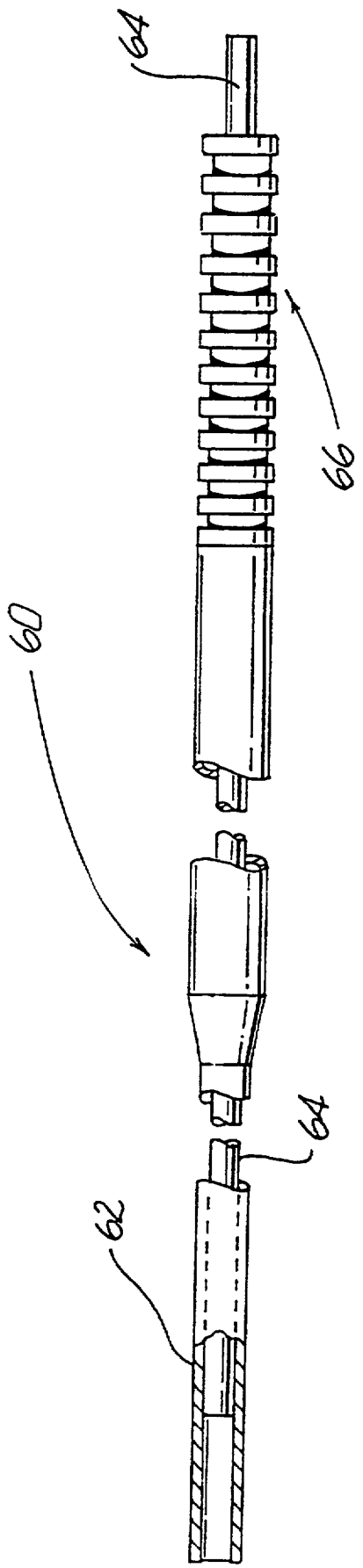
Figure 7:
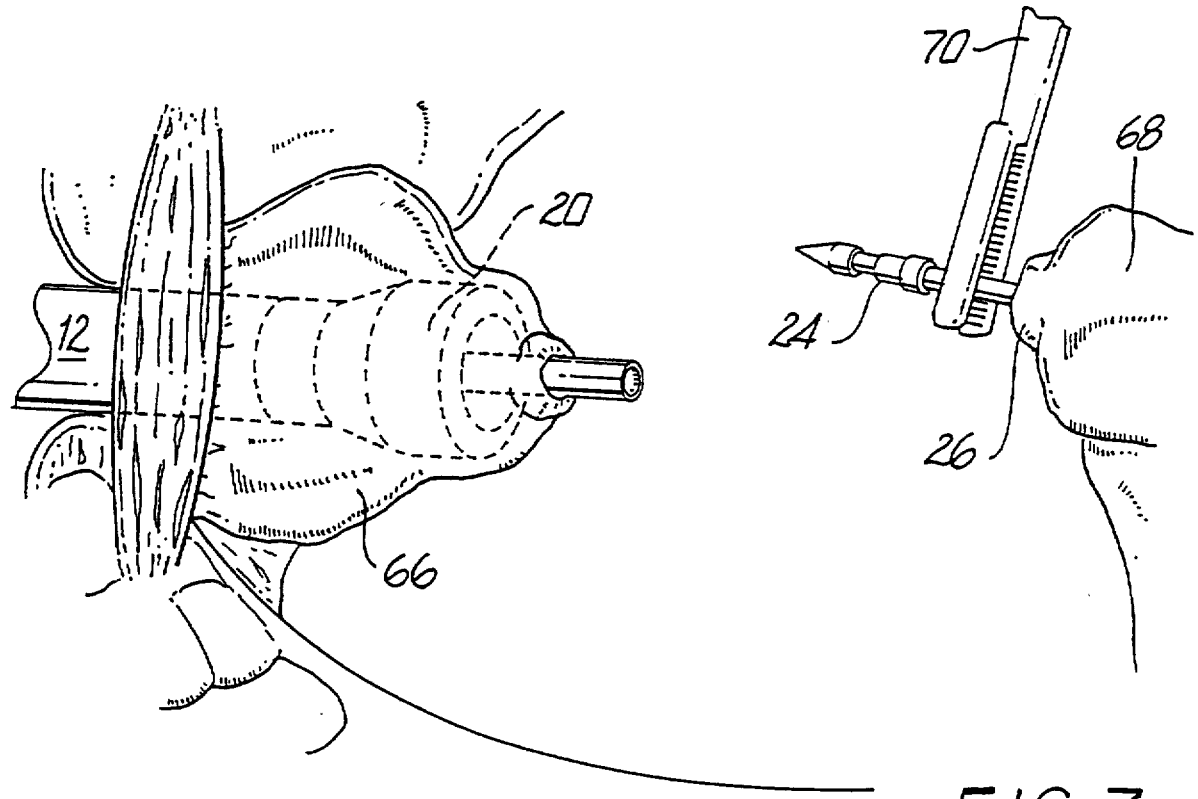
Figure 8:
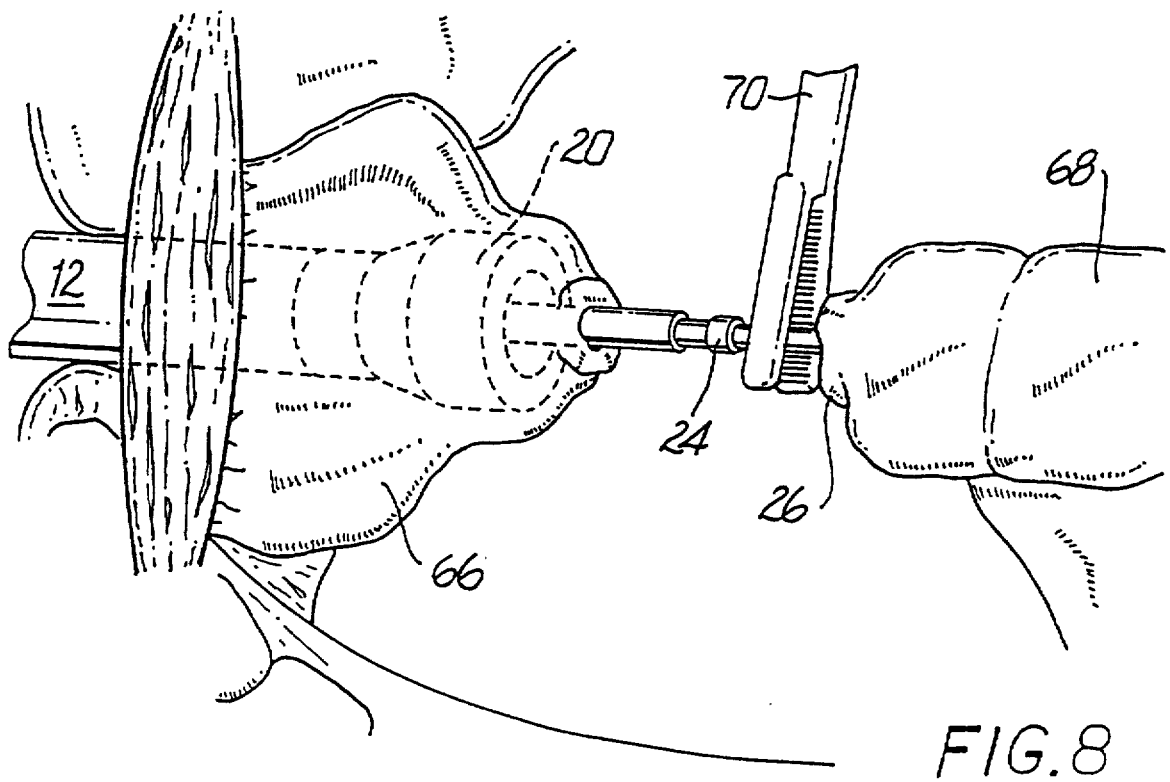

Referring now to FIGS. 4, 5A and 5B, anvil rod 24 is illustrated with anvil head 26 mounted on collar 40 so as to illustrate the advantages of the novel pivoting feature of distal end portion 38. The pivoting feature of distal end portion 38 facilitates introduction and manipulation of anvil assembly 22 within tubular organ tissue such as the colon, intestines, etc. by orienting anvil head 26 in a manner which reduces the profile of the anvil head and the anvil assembly as the assembly is being advanced through the tubular organ. In particular, when distal end portion 38 is in a generally aligned position as shown in FIG. 4, which position corresponds to the orientation of a conventional anvil assembly, the anvil assembly 22 presents a relatively large cross-sectional dimension or profile which must pass through the tubular organ. Specifically, the dimension or profile is equal to the diameter of the anvil head, which in many instances, is greater than the corresponding inner dimension of the tubular organ in which it must pass. Consequently, anvil head 26 inherently engages the inner wall of the tubular organ during manipulation and advancement of the anvil assembly 22 and, accordingly, impedes such advancement within the tubular organ.

Referring now to FIGS. 5A and 5B, when distal end portion 38 is pivoted to its transverse position by way of the pivoting feature of the present invention, the effective transverse cross-sectional dimension or profile of anvil assembly 22 is substantially reduced. In particular, since anvil head 26 is generally parallel to and flush with anvil rod 24 in this position, the effective transverse cross-sectional dimension of assembly 22 is nearly one-half of the corresponding dimension in the operative position of anvil assembly shown in FIG. 4. It is to be appreciated that distal end portion 38 may be pivoted through a variety of angles relative to the anvil rod and still present a cross-sectional dimension or profile which is less than that of the generally aligned position of the distal end portion shown in FIG. 4.

In use, distal end portion 38 may be pivoted prior to introduction of anvil assembly within the tubular organ or may be initially inserted in a generally aligned position in which it subsequently assumes a pivoted position during advancement through the tubular organ due to engagement of anvil head 26 with the inner wall of the tubular organ.

In performing intestinal surgery such as a colonoscopy or a colectomy in which the surgery is followed by anastomosis of hollow tubular organs, anvil assembly 22 may be introduced into the hollow organ through a surgically provided incision, or transanally, and advanced to a predetermined location in the intestinal section so that the anvil assembly may be subsequently mounted to a stapling apparatus to complete the anastomosis.

Figure 6:
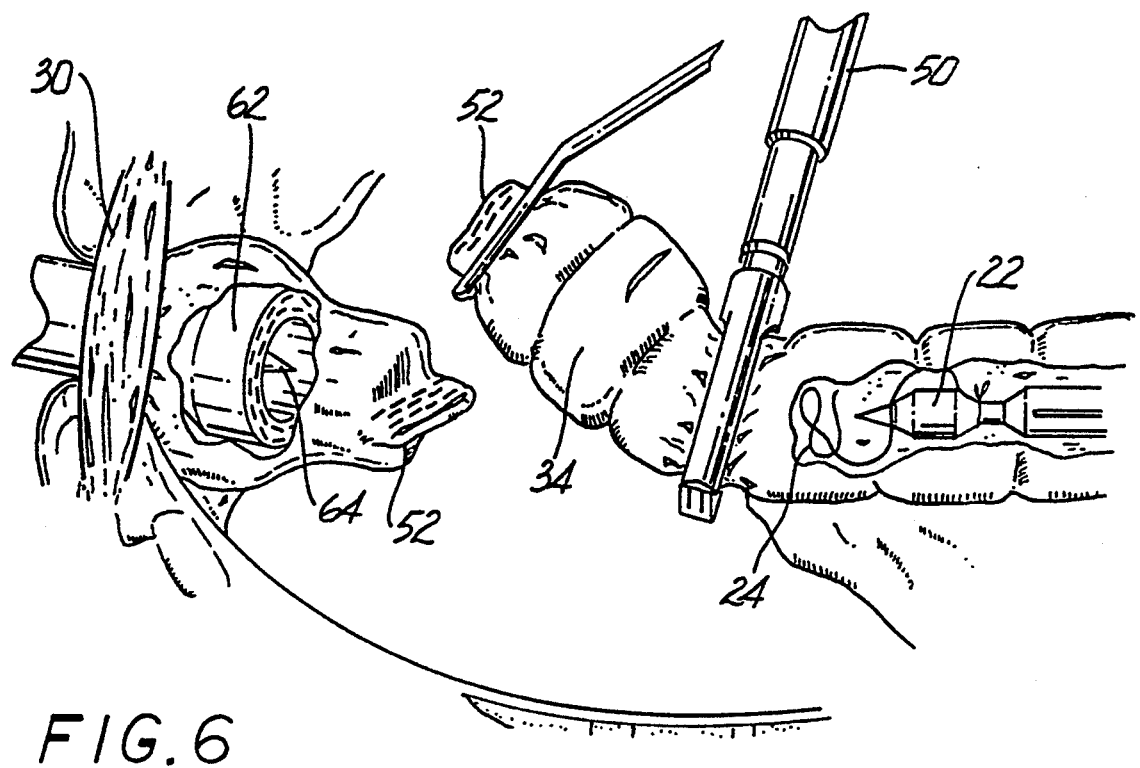
FIG. 6 is a side view of a delivery system used to deliver the anvil rod to a desired predetermined location within a tubular organ.

Referring now to FIG. 6, there is illustrated an apparatus which may be used to deliver anvil assembly 22 of the present invention to a predetermined desired location within a tubular organ section. This delivery system is disclosed in commonly assigned U.S. patent application Ser. No. 07/886,040, filed May 19, 1992, the contents of which have been incorporated herein by reference. System 60 is particularly adapted to deliver an anvil assembly transanally to a desired portion in the colon and includes an elongated sheath member 62 having a longitudinal bore, a pusher rod 64 slidably movable within the bore of the sheath member and hand grip member 66.

In use with the anvil assembly 22 of the present invention, anvil rod 24 is inserted within the distal end of sheath 62 to mount the assembly to the system. Thereafter, distal end portion 38 is pivoted to the position shown in either FIGS. 5A or 5B to reduce the effective transverse cross-sectional dimension of the anvil assembly 22. The delivery system is inserted transanally and advanced through the colon to a predetermined desired location in the organ, preferably beyond the diseased section of tissue. The particular orientation of anvil head 24 facilitates introduction and advancement of anvil assembly 22 within the intestinal section. Thereafter, the delivery system is actuated by depressing the proximal end section 64a of pusher rod 64, which extends beyond the proximal end of sheath 62, to advance the pusher rod such that it engages anvil rod 24 and expels the anvil assembly 22 from delivery system 60 and beyond the diseased tissue section. Once anvil assembly 22 is within the organ, the surgeon may perform the desired surgery followed by anastomosis of the hollow organ section.

Figure 7:
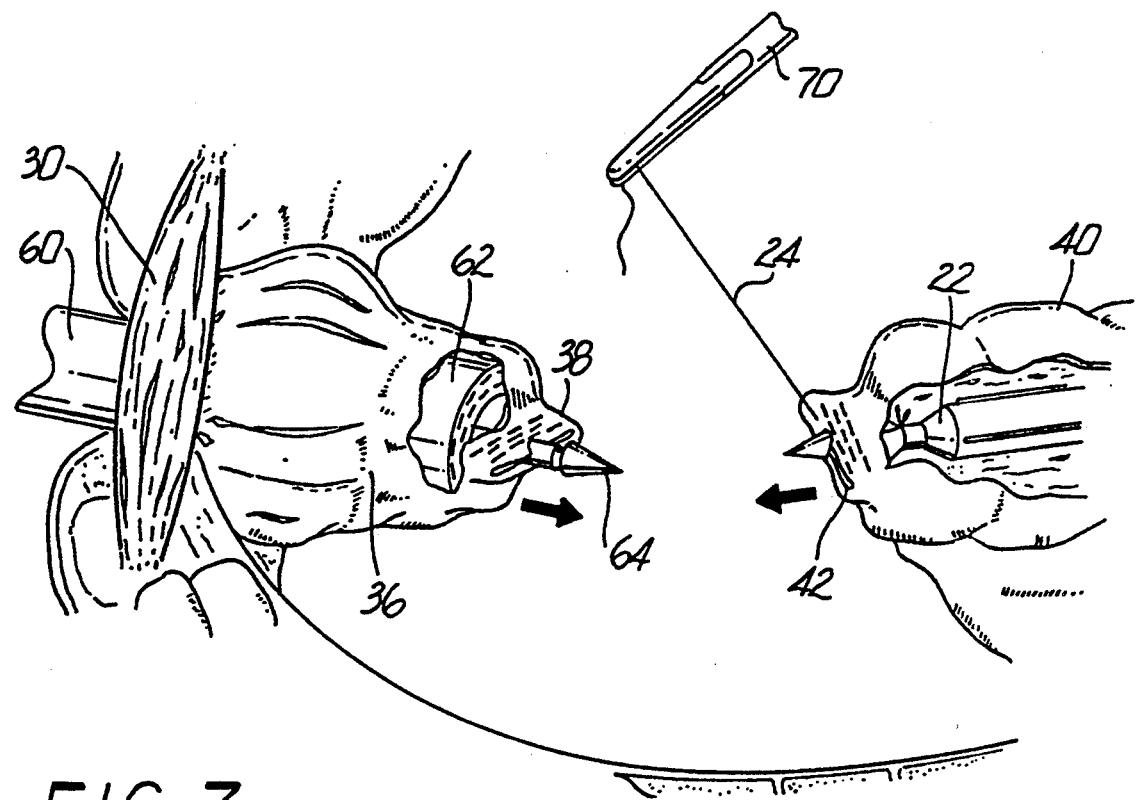
FIG. 7 is a perspective view of the intestinal area of a patient illustrating the introduction of the surgical apparatus of FIG. 1 prior to mounting of the anvil rod of the present invention to the apparatus.
Figure 8:
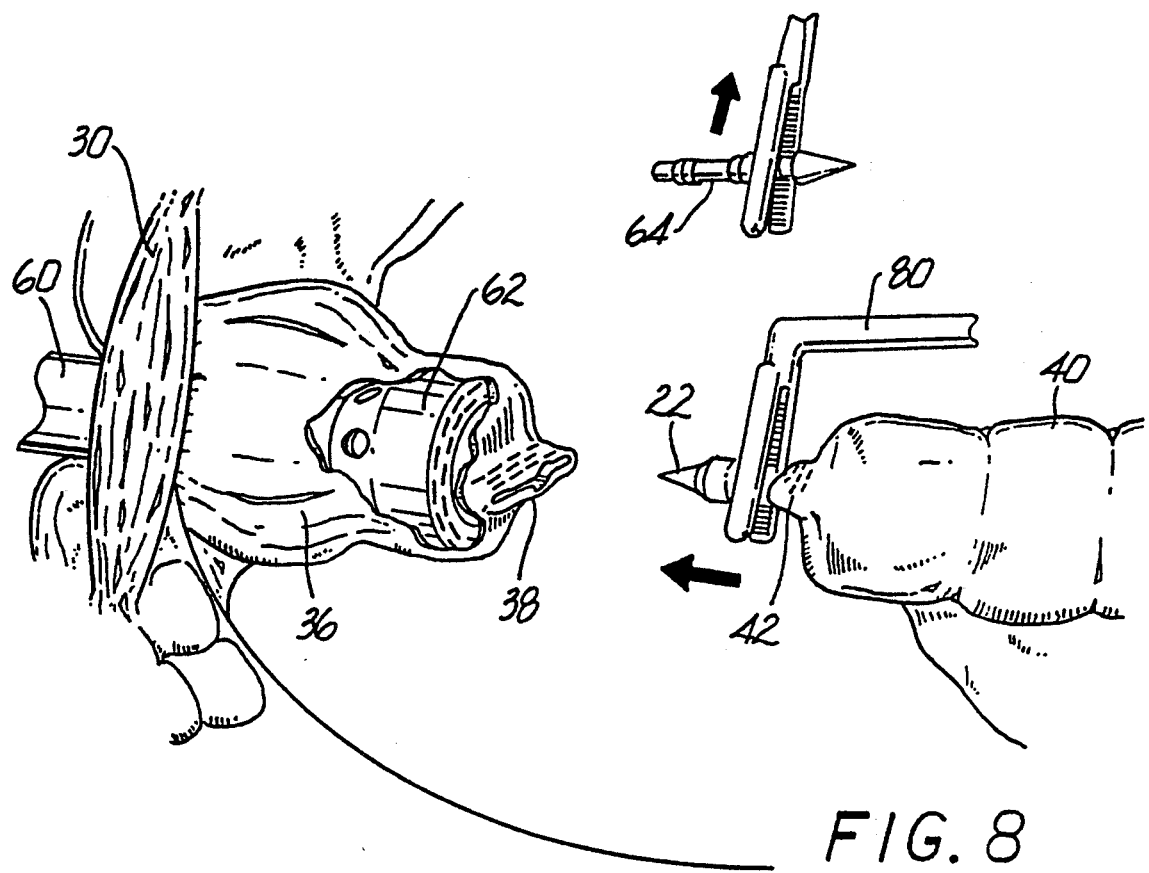
FIG. 8 is a perspective view similar to that of FIG. 7 illustrating mounting of the anvil rod of the present invention to the distal end of the surgical apparatus.
Figure 9:
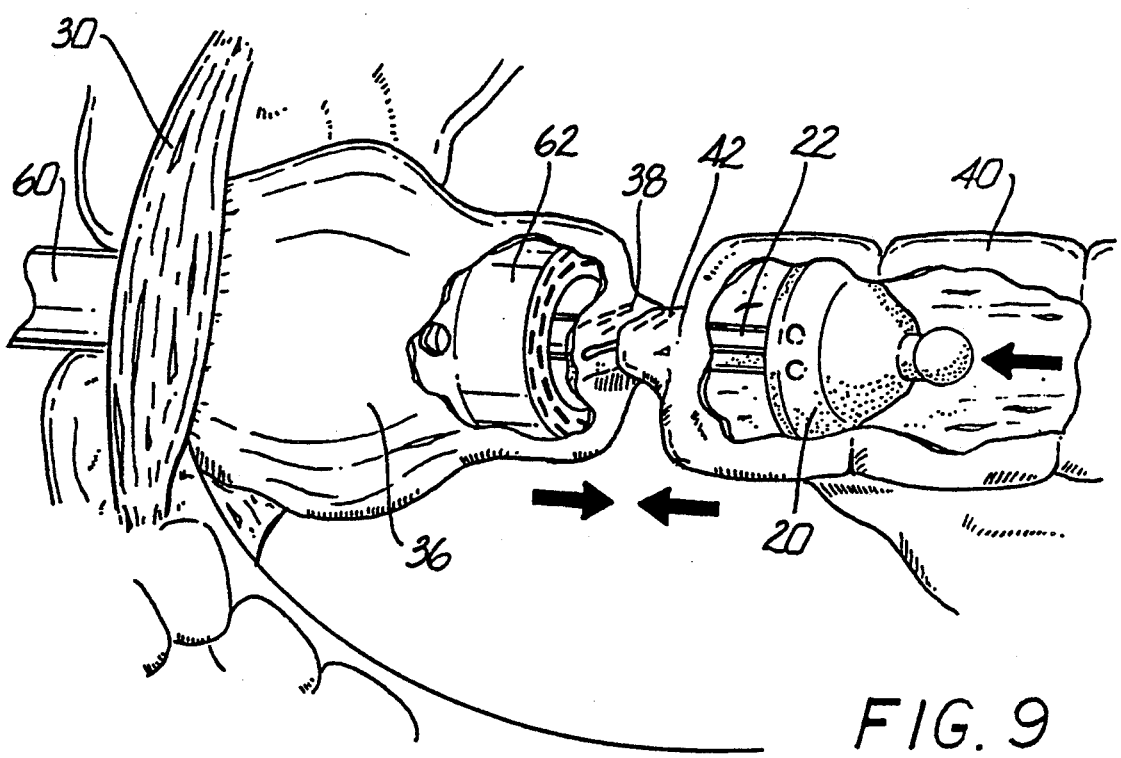
Figure 10:
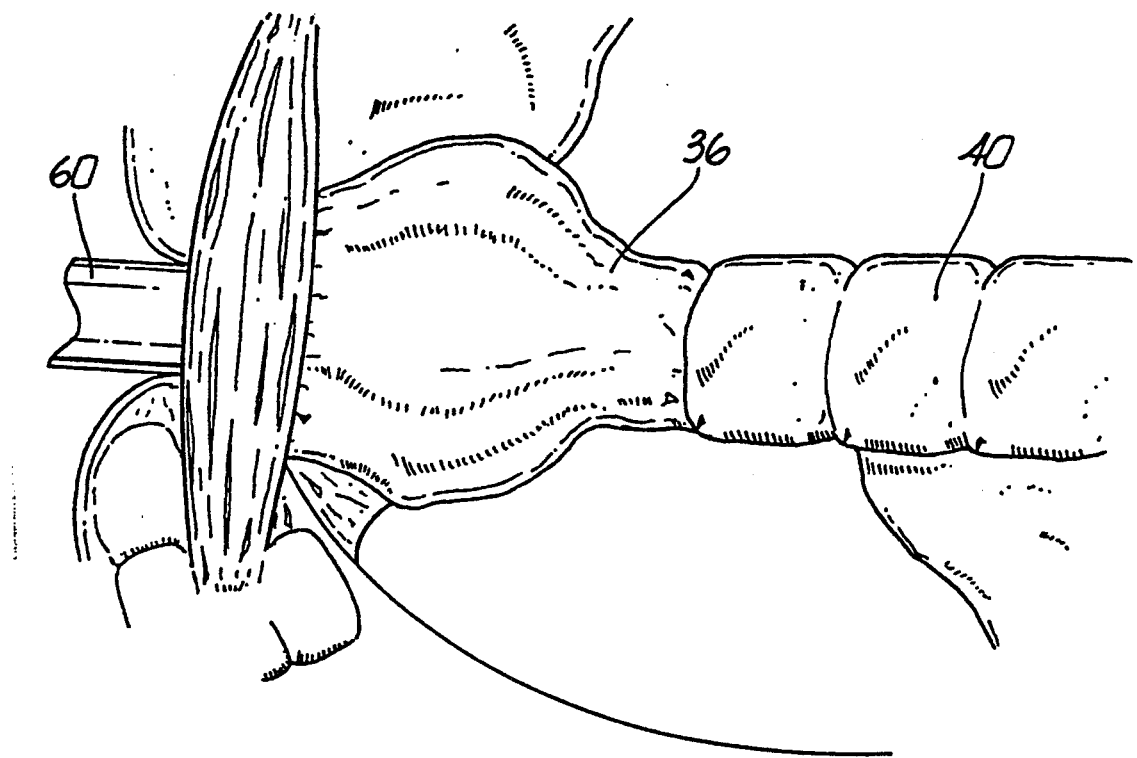
Figure 11:
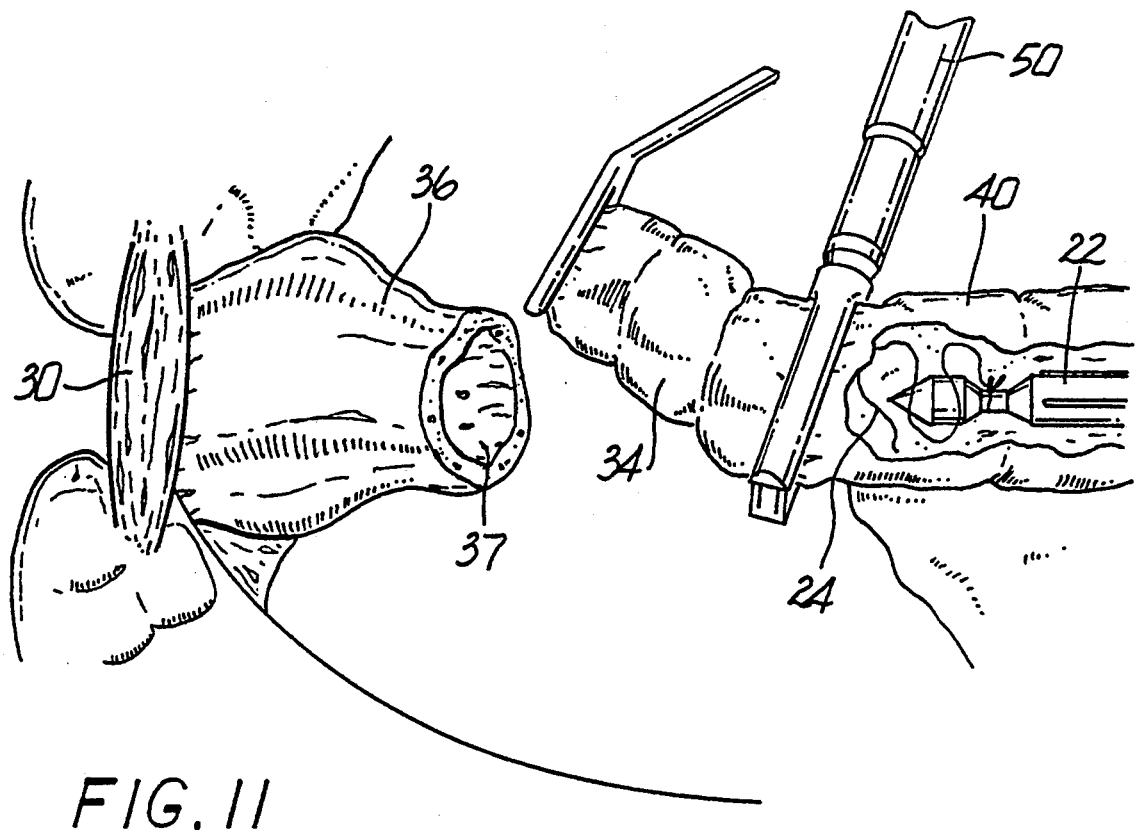
Figure 12:
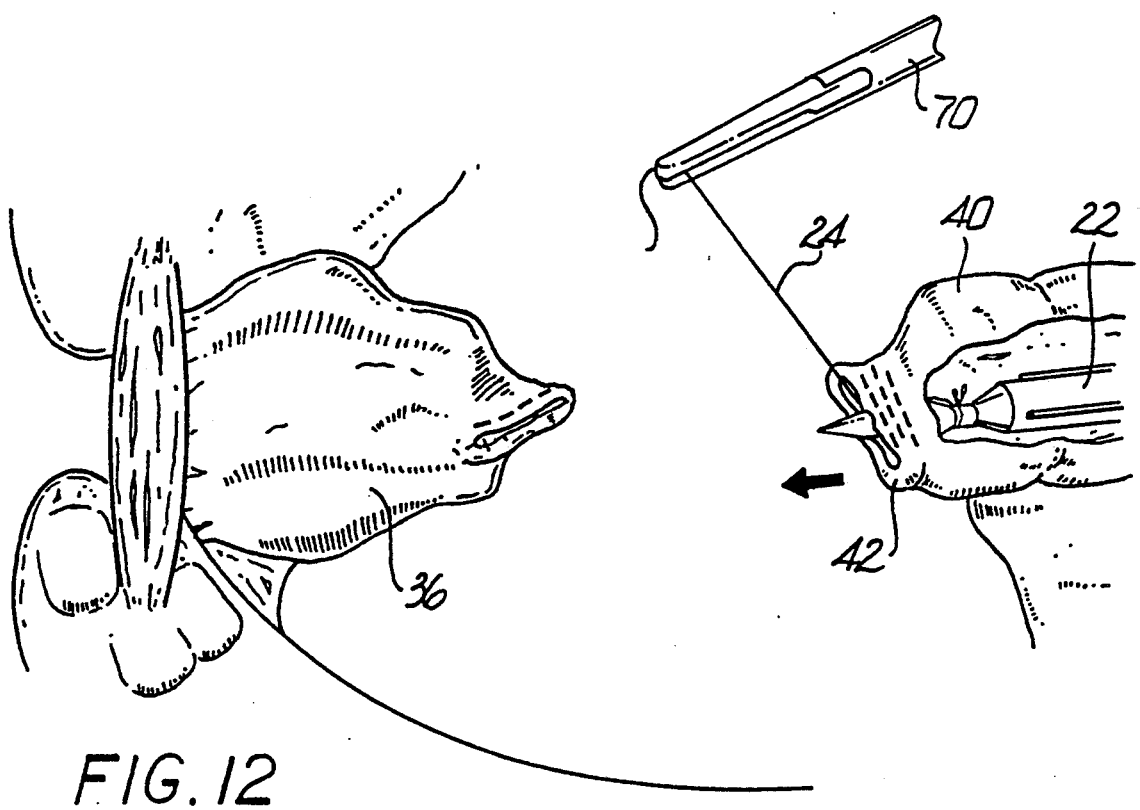

FIGS. 7 and 8 illustrate the use of apparatus 10 and detachable anvil rod 24 in an anastomosis procedure to effect joining of intestinal sections 66, 68. Preferably, the anastomosis procedure is performed using minimally invasive surgical techniques including laparoscopic means and instrumentation. At the point in the procedure shown in FIG. 7, a diseased intestinal section had been previously removed preferably with a laparoscopic instrument applied to the operative site through an appropriate trocar sleeve. Elongated shaft 12 of apparatus 10 had been inserted transanally into intestinal section 66. Both intestinal sections 66, 68 are also shown temporarily secured about their respective components by conventional means such as a purse string stitch.

In completing the anastomosis, the surgeon through an appropriate trocar sleeve probes within the intestinal section to grasp anvil rod 24, preferably with a grasping instrument 70 inserted within a cannula, and maneuvers rod 24 towards the distal end of elongated shaft 12. Mounting portion 30 of rod 24 is then inserted within the distal end of elongated shaft 12 of the apparatus, as shown in FIG. 8, wherein the mounting mechanism within the distal end of the shaft engages the rod to effect the mounting. Thereafter, the anvil assembly and elongated shaft are approximated to clamp the opposed end portions of tissue between anvil head 26 and fastener retainer component 20. Such approximation will also appropriately orientate the anvil head 26 with the apparatus. The apparatus is fired to complete the anastomosis.

The anvil assembly and associated delivery system of the present invention enhances the surgeon's ability to perform intestinal surgery and anastomosis of tissue sections under laparoscopic guidance at least in part by reducing the profile of the assembly so as to facilitate introduction and advancement of the assembly within relatively narrowly dimensioned tubular organ tissue.

Although the present invention has been shown and described in terms of preferred embodiments, it will be appreciated that various changes and other modifications are contemplated within the spirit and scope of the present invention as defined by the following claims.

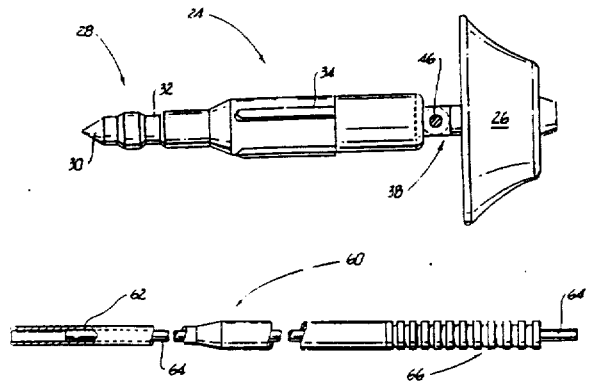

What is claimed is:

1. A surgical system for delivering an anvil assembly within a hollow tubular organ, comprising:
   a) an anvil assembly for use with an apparatus for performing circular anastomosis, said anvil assembly comprising an elongated anvil rod having a proximal end portion for mounting to an apparatus for performing circular anastomosis, a distal end portion defining a longitudinal axis, and a generally hemisphericalshaped anvil head having an arcuate anvil surface for forming staples ejected by the apparatus, said anvil head defining a central axis and being coaxially mounted to said distal end portion of said anvil rod, said distal end portion being pivotal between a first position and a second position whereby at least one dimension of said anvil assembly in said second position is effectively less than the corresponding dimension in said first position; and
   b) an elongated delivery member positionable within a hollow tubular organ, said elongated delivery member including mounting means for releasably mounting said proximal end portion of said anvil rod of said anvil assembly thereto and releasing means for releasing said anvil assembly therefrom.

2. The surgical system according to claim 1 wherein said distal end portion of said anvil rod is pivotal with respect to a longitudinal axis defined by said proximal end portion of said anvil rod through an angle of up to about 90°.

3. The surgical system according to claim 2 wherein said distal end portion said anvil rod is adapted to pivot up to about 90° with respect to said longitudinal axis of said proximal end portion in a first direction and up to about 90° with respect to said longitudinal axis of said proximal end portion in a second direction, whereby full pivotal articulation thereof is provided of about 180°.

4. A surgical system for delivering an anvil assembly within a hollow tubular organ, comprising:
   a) an anvil assembly for use with an apparatus for performing circular anastomosis, said anvil assembly comprising an elongated anvil rod having a proximal end portion for mounting to an apparatus for performing circular anastomosis, a distal end portion defining a longitudinal axis and a generally hemispherical-shaped anvil head defining an arcuate anvil surface for forming staples ejected by the apparatus, said anvil head defining a central axis and being coaxially mounted to said distal end portion of said anvil rod, said proximal end portion defining a longitudinal axis, said distal end portion of said anvil rod being pivotal between a first operative position wherein said longitudinal axis of said distal end portion is in general alignment with said longitudinal axis of said proximal end portion and a second non-operative position wherein said longitudinal axis of said distal end portion is angularly displaced relative to said longitudinal axis of said proximal end portion; and
   b) an elongated delivery member positionable within a hollow tubular organ, said delivery member including:
   proximal and distal end portions;
      mounting means associated with said distal end portion of said delivery member for releasably mounting said proximal end portion of said anvil rod of said anvil assembly; and
      releasing means for releasing said anvil assembly from said mounting means.

5. The surgical system according to claim 4 wherein said anvil rod of said anvil assembly comprises a plurality of longitudinally extending external splines disposed intermediate said proximal and distal end portions, said external splines engagable with cooperating longitudinally extending internal splines formed within a distal end of an apparatus for performing circular anastomosis to properly align said anvil rod with the apparatus.

6. A surgical system for delivering an anvil assembly within a hollow tubular organ comprising:
   a) an anvil assembly for use with an apparatus for performing circular anastomosis, said anvil assembly comprising an anvil rod having proximal and distal end portions and an anvil head mounted to said distal end portion, said proximal end portion including a conical shaped mounting portion to facilitate mounting of said anvil rod to an apparatus for performing circular anastomosis, said proximal end portion defining a longitudinal axis, said distal end portion being pivotable between a first position and a second position wherein at least one dimension of said anvil assembly in said second position is effectively less than the corresponding dimension in said first position; and
   b) an elongated delivery member positionable within a hollow tubular organ, said delivery member including mounting means for releasably mounting said proximal end portion of said anvil rod of said anvil assembly thereto and releasing means for releasing said anvil assembly therefrom.

7. The surgical system according to claim 6 wherein said distal end portion of said anvil rod is pivotal with respect to said longitudinal axis defined by said proximal end portion of said anvil rod through an angle of up to about 90°.

8. The surgical system according to claim 7 wherein said distal end portion of said anvil rod is adapted to pivot up to about 90° with respect to said longitudinal axis in a first direction and up to about 90° with respect to said longitudinal axis in a second direction, whereby full pivotal articulation thereof is provided of about 180°.

9. The surgical system according to claim 6 wherein said distal end portion of said anvil rod comprises a circumferential mounting collar, said mounting collar being received within a circular aperture formed within said anvil head to mount said anvil head to said anvil rod.

10. The surgical system according to claim 9 wherein said mounting collar comprises a plurality of longitudinally extending external splines engagable with cooperating longitudinally extending internal splines formed within said anvil head to properly align said anvil head with said anvil rod.

11. The surgical system according to claim 6 wherein said elongated delivery member defines proximal and distal end portions and includes a longitudinal bore extending therethrough.

12. The surgical system according to claim 11 wherein said anvil rod of said anvil assembly is positioned within said distal end portion of said delivery member and within said longitudinal bore to releasably mount said anvil assembly to said delivery member.

13. The surgical system according to claim 12 wherein said anvil rod is configured and dimensioned to form a friction fit between an outer peripheral surface of said anvil rod and an inner peripheral wall of said delivery member to releasably mount said anvil assembly to said distal end portion of said delivery member.

14. The surgical apparatus of claim 12 wherein said releasing means comprises a rod member having proximal and distal end portions, said rod member received within said longitudinal bore of said elongated delivery member and distally advanceable relative to said delivery member such that a bearing surface disposed at said distal end portion of said rod member engages said anvil rod of said anvil assembly to effect distal displacement of said anvil assembly and release of said anvil assembly from said distal end portion of said delivery member.

15. A surgical system for delivering an anvil assembly within a hollow tubular organ, comprising:

a) an anvil assembly for use with an apparatus for performing circular anastomosis, said anvil assembly comprising an elongated anvil rod having a proximal end portion for mounting to an apparatus for performing circular anastomosis, a distal end portion defining a longitudinal axis and a generally hemispherical-shaped anvil head defining an arcuate anvil surface for forming staples ejected by the apparatus, said anvil head defining a central axis and being coaxially mounted to said distal end portion of said anvil rod, said proximal end portion defining a longitudinal axis, said distal end portion of said anvil rod being pivotal between a first operative position wherein said longitudinal axis of said distal end portion is in general alignment with said longitudinal axis of said proximal end portion and a second nonoperative position wherein said longitudinal axis of said distal end portion is angularly displaced relative to said longitudinal axis of said proximal end portion, said anvil rod including a plurality of longitudinally extending external splines disposed intermediate said proximal and distal end portions, said external splines engageable with cooperating longitudinally extending internal splines formed within a distal end of the apparatus to properly align said anvil rod with the apparatus; and b) an elongated delivery member positionable within a hollow tubular organ, said delivery member including:

proximal and distal end portions;

mounting means associated with said distal end portion of said delivery member for releasably mounting said proximal end portion of said anvil rod of said anvil assembly; and releasing means for releasing said anvil assembly from said mounting means.

* * * * *

UNITED STATES PATENT AND TRADEMARK OFFICE
CERTIFICATE OF CORRECTION

PATENT NO. : 5,344,059
DATED : September 6, 1994
INVENTOR(S) : David T. Green

It is certified that error appears in the above-indentified patent and that said Letters Patent is hereby corrected as shown below:

The title page should be deleted to appear as per attached title page.

Figures 1-12 should be deleted to be replaced with figures 1-8 as shown on the attached sheets.

Signed and Sealed this

Seventeenth Day of January, 1995

Attest:

BRUCE LEHMAN

*Attesting Officer*      *Commissioner of Patents and Trademarks*

United States Patent [19]

Green et al.

[11] Patent Number: 5,344,059
[45] Date of Patent: Sep. 6, 1994

[54] SURGICAL APPARATUS AND ANVIL DELIVERY SYSTEM THEREFOR

[75] Inventors: David T. Green, Westport; Henry Bolanos, East Norwalk; Henry R. Sienkiewicz, Stamford, all of Conn.; Patrick Leahy, Dublin, Ireland

[73] Assignee: United States Surgical Corporation, Norwalk, Conn.

[21] Appl. No.: 950,435

[22] Filed: Sep. 23, 1992

Related U.S. Application Data

[63] Continuation-in-part of Ser. No. 886,040, May 19, 1992.

[51] Int. Cl.$^5$ ............................................. A61B 17/115
[52] U.S. Cl. ............................................. 227/179; 227/19
[58] Field of Search ................... 227/19, 179, 175, 176, 227/178

[56] References Cited

U.S. PATENT DOCUMENTS

| | | |
|---|---|---|
| 3,193,165 | 7/1965 | Akhalaya et al. . |
| 3,593,903 | 7/1971 | Astafiev et al. . |
| 4,198,982 | 4/1980 | Fortner et al. . |
| 4,304,236 | 12/1981 | Conta et al. . |
| 4,319,576 | 2/1986 | Rothfuss . |
| 4,379,457 | 4/1983 | Gravener et al. . |
| 4,473,077 | 9/1984 | Noiles et al. . |
| 4,476,863 | 10/1984 | Kanshin et al. . |
| 4,505,272 | 3/1985 | Utyamyshev . |
| 4,537,193 | 8/1985 | Tanner . |
| 4,566,620 | 1/1986 | Green et al. .............. 227/19 |
| 4,573,468 | 3/1986 | Conta et al. . |
| 4,576,167 | 3/1986 | Noiles . |
| 4,603,693 | 8/1986 | Conta et al. . |
| 4,646,745 | 3/1987 | Noiles . |
| 4,671,445 | 6/1987 | Barker et al. .............. 227/19 |
| 4,817,847 | 4/1989 | Redtenbacher et al. . |
| 4,848,367 | 7/1989 | Avant et al. . |
| 4,873,977 | 10/1989 | Avant et al. . |
| 5,104,025 | 4/1992 | Main et al. . |
| 5,108,420 | 4/1992 | Marks . |
| 5,119,983 | 6/1992 | Green et al. . |
| 5,122,156 | 6/1992 | Green et al. . |
| 5,139,513 | 8/1992 | Segato ....................... 227/179 X |
| 5,271,543 | 12/1993 | Grant et al. ................ 227/19 X |

FOREIGN PATENT DOCUMENTS

| | | |
|---|---|---|
| 1136020 | 12/1979 | Canada . |
| 0190022 | 8/1986 | European Pat. Off. . |
| 282157 | 9/1988 | European Pat. Off. . |
| 1057729 | 5/1959 | Fed. Rep. of Germany . |
| 3301713 | 7/1984 | Fed. Rep. of Germany . |
| 1461464 | 12/1966 | France . |
| 1588250 | 4/1970 | France . |
| 2443239 | 12/1979 | France . |
| 7711347 | 4/1979 | Netherlands . |
| WO8706448 | 11/1987 | PCT Int'l Appl. . |
| WO9006085 | 6/1990 | PCT Int'l Appl. . |

OTHER PUBLICATIONS

"Use of the Stapler in Interior Reception for Cancer of the Rectosigmoid", Resnick et al., Israel Journal of Medical Sciences, vol. 19, 1983, pp. 128–133.

"New Method of Bowel Stoma Formation", American Journal of Surgery, vol. 152, Nov. 1986, pp. 545–548.

EEA Anvil with a Separate Short-Shaft-Non Confidential Disclosure Agreement-Sep. 1981.

"Minimally Invasive Colon Resection (Laparoscopic Colectomy)", Jacobs et al., Surgical Laparoscopy & Endoscopy, vol. 1, No. 3, Sep. 1991, pp. 144–150.

U.S. Surgical Corporation, "Auto Suture Information Booklet" 1990.

Primary Examiner—Rinaldi I. Rada

[57] ABSTRACT

A detachable anvil assembly for use with an apparatus for performing circular anastomosis of tubular organs includes an elongated anvil rod having proximal and distal end portions and an anvil head mounted to the distal end portion of the anvil rod. The distal end portion is pivotally mounted and is adapted to pivot approximately plus or minus ninety degrees relative to a longitudinal axis defined by the rod. An elongated delivery member detachably receives the anvil assembly and facilitates delivery of the anvil assembly to the operative site. The pivoting feature of the distal end reduces the transverse profile of the assembly which consequently facilitates introduction and advancement of the anvil assembly within the tubular organ.

15 Claims, 6 Drawing Sheets